(12) United States Patent
Sakaguchi

(10) Patent No.: US 9,907,710 B2
(45) Date of Patent: Mar. 6, 2018

(54) DISPOSABLE DIAPER

(71) Applicant: UNICHARM CORPORATION, Shikokuchuo-shi, Ehime (JP)

(72) Inventor: Satoru Sakaguchi, Kanoji (JP)

(73) Assignee: UNICHARM CORPORATION, Ehime (JP)

( * ) Notice: Subject to any disclaimer, the term of this patent is extended or adjusted under 35 U.S.C. 154(b) by 796 days.

(21) Appl. No.: 14/359,741

(22) PCT Filed: Nov. 21, 2012

(86) PCT No.: PCT/JP2012/080183
§ 371 (c)(1),
(2) Date: May 21, 2014

(87) PCT Pub. No.: WO2013/077361
PCT Pub. Date: May 30, 2013

(65) Prior Publication Data
US 2014/0330239 A1    Nov. 6, 2014

(30) Foreign Application Priority Data

Nov. 22, 2011  (JP) .................................. 2011-255254

(51) Int. Cl.
*A61F 13/15* (2006.01)
*A61F 13/49* (2006.01)
(Continued)

(52) U.S. Cl.
CPC ...... *A61F 13/49001* (2013.01); *A61F 13/536* (2013.01); *A61F 13/49017* (2013.01);
(Continued)

(58) Field of Classification Search
CPC .......... A61F 13/49017; A61F 13/49019; A61F 2013/49084; A61F 2013/49085;
(Continued)

(56) References Cited

U.S. PATENT DOCUMENTS 6,387,085 B1 * 5/2002 Van Gompel ........... A61F 13/84
604/307
7,972,319 B2    7/2011 Umebayashi et al.
(Continued)

FOREIGN PATENT DOCUMENTS

CN    101166433 A    4/2008
JP    2001-037807    2/2001
(Continued)

OTHER PUBLICATIONS

Office Action in CN Patent Application No. 201280057492.7, dated May 6, 2016.
(Continued)

*Primary Examiner* — Jacqueline Stephens
(74) *Attorney, Agent, or Firm* — Hauptman Ham, LLP

(57) ABSTRACT

A disposable diaper includes: a first inflected unit formed in an absorber and extending along a product widthwise direction; a second inflected unit formed in the absorber, extending along the product widthwise direction, and positioned towards a rear waistline unit from the first inflected unit; and a crotch unit formed between the first inflected unit and the second inflected unit. The size of the crotch unit along the product longitudinal direction is 30 mm or more and 150 mm or less in the natural state of the disposable diaper.

15 Claims, 7 Drawing Sheets

(51) Int. Cl.
*A61F 13/536* (2006.01)
*A61F 13/53* (2006.01)
*A61F 13/534* (2006.01)

(52) U.S. Cl.
CPC .............. *A61F 13/49019* (2013.01); *A61F 2013/49038* (2013.01); *A61F 2013/49063* (2013.01); *A61F 2013/49084* (2013.01); *A61F 2013/49085* (2013.01); *A61F 2013/530437* (2013.01); *A61F 2013/53463* (2013.01)

(58) Field of Classification Search
CPC .. A61F 2013/49063; A61F 2013/49038; A61F 2013/530437
See application file for complete search history.

(56) References Cited

U.S. PATENT DOCUMENTS

2006/0122570 A1* 6/2006 Kasai .................. A61F 13/532
604/385.24
2009/0312739 A1 12/2009 Umebayahi et al.

FOREIGN PATENT DOCUMENTS

| | | |
|---|---|---|
| JP | 2004-057413 | 2/2004 |
| JP | 2008-012197 | 1/2008 |
| TW | 200916067 A | 4/2009 |
| WO | WO2006118214 A1 | 11/2006 |

OTHER PUBLICATIONS

Office Action in AU Patent Application No. 2012341538, dated May 25, 2016.
Office Action in TW Patent Application No. 101142025, dated May 17, 2016.
Extended European Search Report dated Jul. 20, 2015, corresponding to European patent application No. 12851779.4.
Office Action in JP Application No. 2013-119699, dated Feb. 9, 2016.
Office Action in Egyptian Application No. 2014050816, dated Feb. 11, 2016.
Office Action dated Apr. 23, 2015, corresponding to Chinese patent application No. 201280057492.7.
Office Action in CN Application No. 201280057492.7, dated Nov. 19, 2015.
Japanese Office Action for Japanese Patent Application Serial No. 2012-5560303 dated Feb. 5, 2013 w/ English Translation.
International Search Report for PCT/JP2012/080183 dated Feb. 5, 2013 w/ English language translation.
Office Action in CN Patent Application No. 201510542619.X, dated Nov. 28, 2017, 27pp.

* cited by examiner

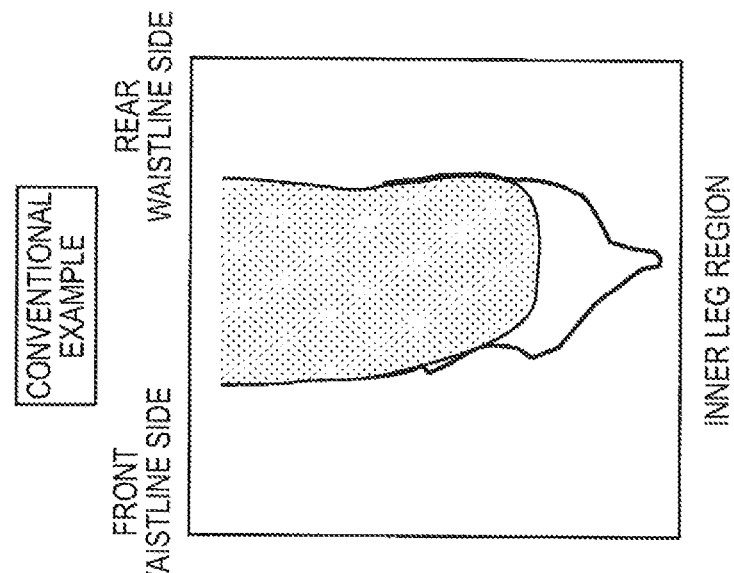
FIG. 5B CONVENTIONAL EXAMPLE
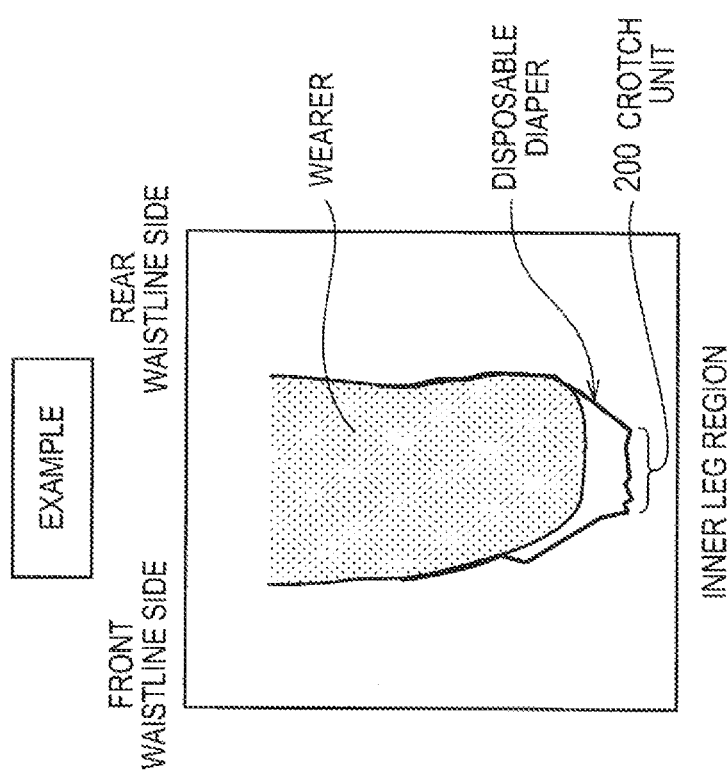
FIG. 5A EXAMPLE

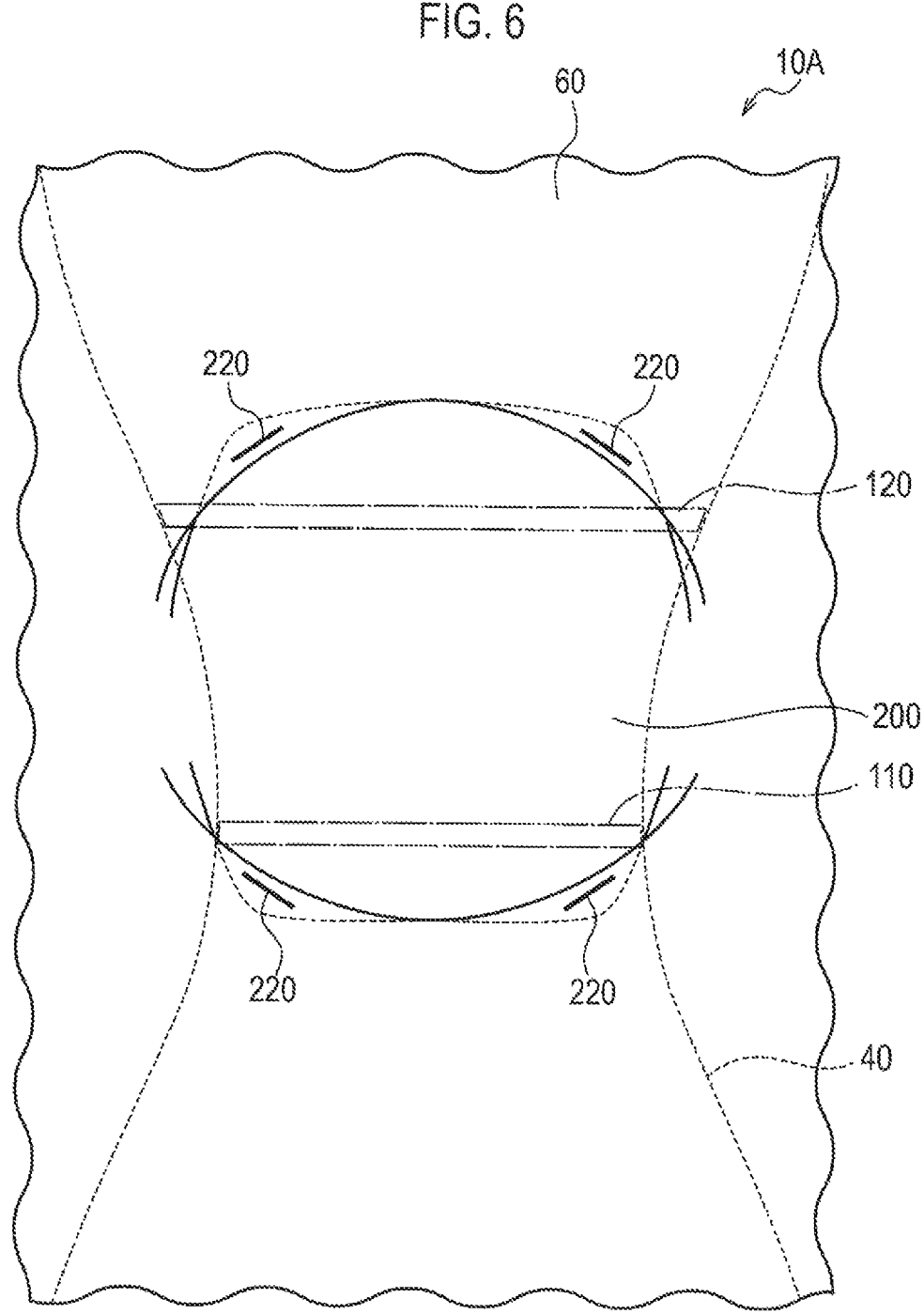

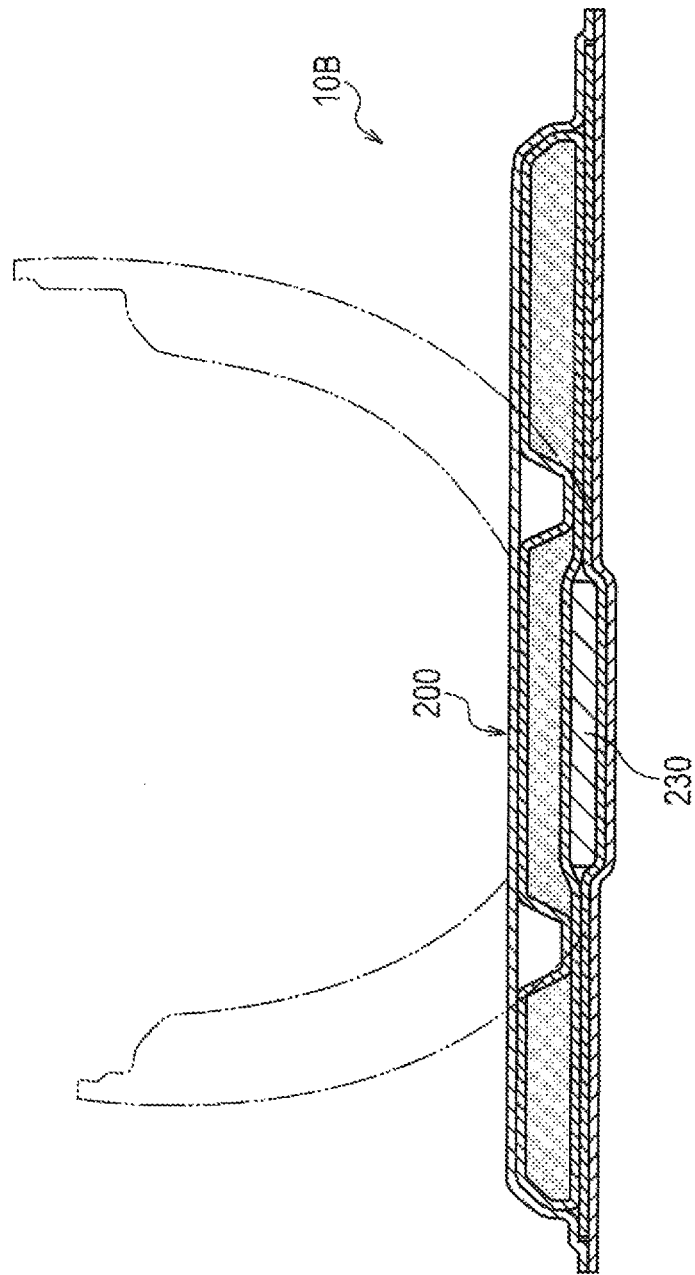

DISPOSABLE DIAPER

RELATED APPLICATIONS

The present application is a National Phase of International Application Number PCT/JP2012/080183, filed Nov. 21, 2012, and claims priority from Japanese Application Number 2011-255254, filed Nov. 22, 2011.

FIELD OF INVENTION

The present invention relates to a disposable diaper including an absorber running across a crotch region and extending in the front waistline region and the rear waistline region.

BACKGROUND ART

Conventionally, in order to achieve a wearing comfort while preventing the leakage of bodily waste, various efforts have been made for a disposable diaper. For example, a disposable diaper is known in which by arranging elastic members along the leg hole opening units, the pressure marks due to the elastic members do not occur easily on the body of the wearer (for example, Patent Literature 1).

Furthermore, generally, such a disposable diaper often employs a structure in which another elastic member is arranged along the waistline opening unit, and the periphery of the leg hole opening units and periphery of the waistline opening unit are tightened. As a result of such a structure, the sagging of the disposable diaper can be prevented even when the disposable diaper absorbs the bodily waste, or the wearer moves actively.

CITATION LIST

Patent Literature

Patent Literature 1: Japanese Unexamined Patent Application Publication No. 2001-37807 (FIG. 1 and FIG. 2)

SUMMARY OF INVENTION

Technical Problem

However, the aforementioned conventional disposable diaper had the below problems. That is, the conventional disposable diaper has a problem that the structure such that mainly the periphery of the leg hole opening units and periphery of the waistline opening unit are tightened does not make it easy in any way to ensure the wearing comfort that would be otherwise achieved in the underwear.

Generally, underwear is made of a material such that the front waistline unit (front body) and the rear waistline unit (rear body) can be expanded and contracted as a whole (can be stretched as a whole). On the other hand, generally, the crotch unit (gusset unit) is not made of a material that can be expanded and contracted so much, and due to the pulling of the crotch unit by the front waistline unit and the rear waistline unit, the crotch unit is also configured to fit the body of the wearer.

However, even in the case of a disposable diaper, if the structure of the crotch unit is made so as to fit the body of the wearer in order to achieve the equivalent wearing comfort that would be otherwise obtained in the underwear, the bodily waste will continue to be in contact with the body, which can easily become a cause of skin problems. Furthermore, if the crotch unit is made to fit the body, there exist other problems in that the density of the absorber rises due to the pressure of the body causing a decline in the speed of absorption of the liquid by the absorber, and a pressure is exerted on the absorber due to the movement of the wearer because of which the liquid returns back to the skin.

Furthermore, in the conventional disposable diaper, an excess space (excess fabric) is provided from the waistline retaining unit up to the crotch region. This is because a disposable diaper would sag down without the ability to follow the extension of the skin due to a change in the posture or movement of the wearer unless an excess space is provided in the crotch region in order to provide a flat absorber for a three-dimensional human body having complex irregularities.

Because an excess space (excess fabric) was provided, the periphery of the leg hole opening units had to be fitted without any space in order to prevent the occurrence of leakage, and a structure that would hold the disposable diaper close to the body, such as an increase in the stretching rate, the rate of expansion and contraction of the elastic members arranged in the leg holes, was needed. That is, the constriction became strong and the excess constriction might have contributed to an unpleasant feeling for the wearer.

Thus, the present invention has been achieved in view of such a condition, and an object thereof is to provide a disposable diaper with which it is possible to ensure a wearing comfort as if to wear the underwear, specifically, a pleasant feeling of wearing the diaper, without hindering the movement of the wearer, while maintaining the comfort and absorption performance after excretion.

Solution to Problem

A first aspect of the present invention is summarized as a disposable diaper (disposable diaper 10) comprising: a front waistline region (front waistline region 20); a rear waistline region (rear waistline region 30); a crotch region (crotch region 25) positioned between the front waistline region and the rear waistline region; a pair of leg hole opening units (leg hole opening units 35); an absorber (absorber 40) running across the crotch region and extending in the front waistline region and rear waistline region; a product longitudinal direction (product longitudinal direction L) from the front waistline region towards the rear waistline region; a product widthwise direction (product widthwise direction W) that is perpendicular to the product longitudinal direction; a waistline retaining unit (the front waistline region 20, the rear waistline region 30, and a fastening tape 90) extending along the product widthwise direction in the front waistline region and the rear waistline region, and holding the disposable diaper onto a body of a wearer; a crotch unit (crotch unit 200) that is formed in the crotch region and can be expanded and contracted in the product longitudinal direction or the product widthwise direction; a first inflected unit (first inflected unit 110) that is formed in the absorber and that becomes a curved base point of the disposable diaper by extending along the product widthwise direction; and a second inflected unit (second inflected unit 120) that is formed in the absorber, that becomes the curved base point of the disposable diaper by extending along the product widthwise direction, and that is positioned towards the rear waistline unit from the first inflected unit; wherein the crotch unit is provided independently from the waistline retaining unit without intersecting the waistline retaining unit; and a size along the product longitudinal direction of the crotch unit is 30 mm or more and 150 mm or less, in a natural state of the disposable diaper.

A second aspect of the present invention is summarized as a disposable diaper comprising: a front waistline region; a rear waistline region; a crotch region positioned between the front waistline region and the rear waistline; a pair of leg hole opening units; an absorber running across the crotch region and extending in the front waistline region and rear waistline region; a product longitudinal direction from the front waistline region towards the rear waistline region; a product widthwise direction that is perpendicular to the product longitudinal direction; a waistline retaining unit extending along the product widthwise direction in the front waistline region and the rear waistline region, and holding the disposable diaper onto a body of a wearer; a crotch unit formed in the crotch region; a first inflected unit that is formed in the absorber and that becomes a curved base point of the disposable diaper by extending along the product widthwise direction; a second inflected unit that is formed in the absorber, that becomes the curved base point of the disposable diaper by extending along the product widthwise direction, and that is positioned towards the rear waistline unit from the first inflected unit; and an exterior sheet (backsheet 60) arranged on a non-skin contact surface side of the absorber; wherein the crotch unit is provided independently from the waistline retaining unit without intersecting the waistline retaining unit; a size along the product longitudinal direction of the crotch unit is 30 mm or more and 150 mm or less, in a natural state of the disposable diaper; and a dart unit (dart unit 220) configured to pick at least the exterior sheet is formed in the edges of the crotch unit in the product longitudinal direction.

A third aspect of the present invention is summarized as a disposable diaper comprising: a front waistline region; a rear waistline region; a crotch region positioned between the front waistline region and the rear waistline region; a pair of leg hole opening units; an absorber running across the crotch region and extending in the front waistline region and rear waistline region; a product longitudinal direction from the front waistline region towards the rear waistline region; a product widthwise direction that is perpendicular to the product longitudinal direction; a waistline retaining unit extending along the product widthwise direction in the front waistline region and the rear waistline region, and holding the disposable diaper onto a body of a wearer; a crotch unit formed in the crotch region; a first inflected unit that is formed in the absorber and that becomes a curved base point of the disposable diaper by extending along the product widthwise direction; a second inflected unit that is formed in the absorber, that becomes the curved base point of the disposable diaper by extending along the product widthwise direction, and that is positioned towards the rear waistline unit from the first inflected unit, wherein the crotch unit is provided independently from the waistline retaining unit without intersecting the waistline retaining unit; and a size along the product longitudinal direction of the crotch unit is 30 mm or more and 150 mm or less, in a natural state of the disposable diaper; and the crotch unit has a reinforcing sheet (reinforcing sheet 230) configured to reinforce the crotch unit.

A fourth characteristic of the present invention is summarized as a disposable diaper comprising: a front waistline region; a rear waistline region; a crotch region positioned between the front waistline region and the rear waistline region; a pair of leg hole opening units; an absorber running across the crotch region and extending in the front waistline region and rear waistline region; a product longitudinal direction from the front waistline region towards the rear waistline region; a product widthwise direction that is perpendicular to the product longitudinal; a waistline retaining unit extending along the product widthwise direction in the front waistline region and the rear waistline region, and holding the disposable diaper onto a body of a wearer; a crotch unit formed in the crotch region; a first inflected unit that is formed in the absorber and that becomes a curved base point of the disposable diaper by extending along the product widthwise direction; a second inflected unit that is formed in the absorber, that becomes the curved base point of the disposable diaper by extending along the product widthwise direction, and that is positioned towards the rear waistline unit from the first inflected unit; wherein the absorber is configured to be able to bend along the first inflected unit and the second inflected unit; and as compared to the other portions of the absorber, the crotch unit is configured to be able to more easily maintain a flat shape when the disposable diaper is worn.

Advantageous Effects of Invention

According to the characteristic of the present invention, it is possible to provide a disposable diaper with which it is possible to ensure a wearing comfort as if to wear the underwear, specifically, a pleasant feeling of wearing the diaper, without hindering the movement of the wearer, can be achieved while maintaining the comfort and absorption performance after excretion.

BRIEF DESCRIPTION OF DRAWINGS

FIGS. 5a and 5b are a diagram schematically illustrating the result of a CT scan of the state when the disposable diaper 10 according to the embodiment of the present invention and the conventional disposable diaper are worn by a wearer.

FIG. 6 is a diagram illustrating the shape of a crotch unit of a disposable diaper 10A according to a modification of the present invention.

FIG. 7 is a diagram illustrating the shape of a crotch unit of a disposable diaper 10B according to a modification of the present invention.

DESCRIPTION OF EMBODIMENTS

Figure 1:
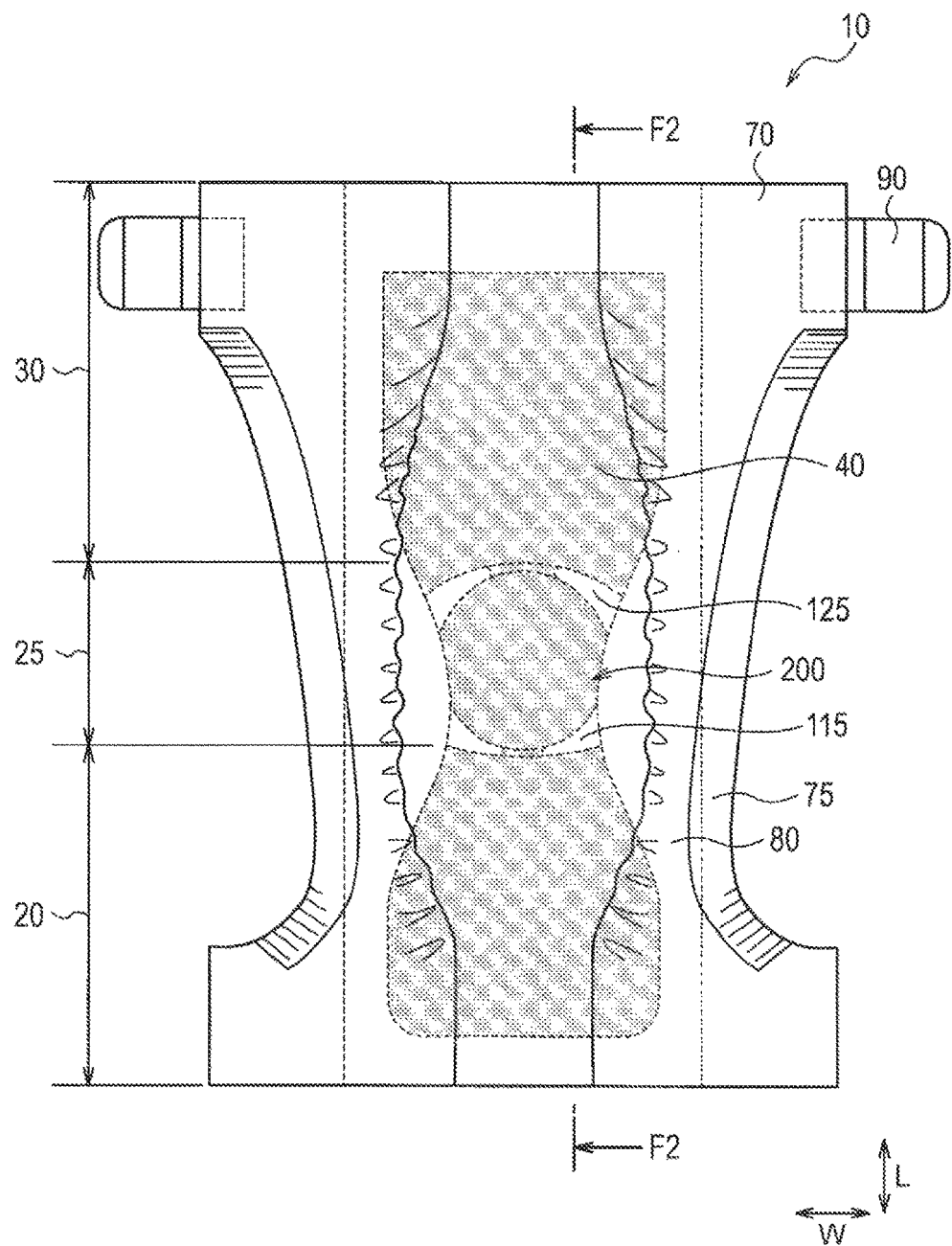
FIG. 1 is an exploded plan view of a disposable diaper 10 according to an embodiment of the present invention.

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Entire Schematic Configuration of Disposable Diaper

FIG. 1 is an exploded plan view of the disposable diaper 10 according to the present embodiment. It should be noted that the exploded plan view of FIG. 1 is a diagram in which leg gathers 75 and leg side gathers 80 are in an elongated state such that wrinkles are not formed in a topsheet 50 and side flap 70, for example, that configure the disposable diaper 10, but for the sake of description, the leg side gathers 80 are illustrated in a stretched state.

Figure 2:
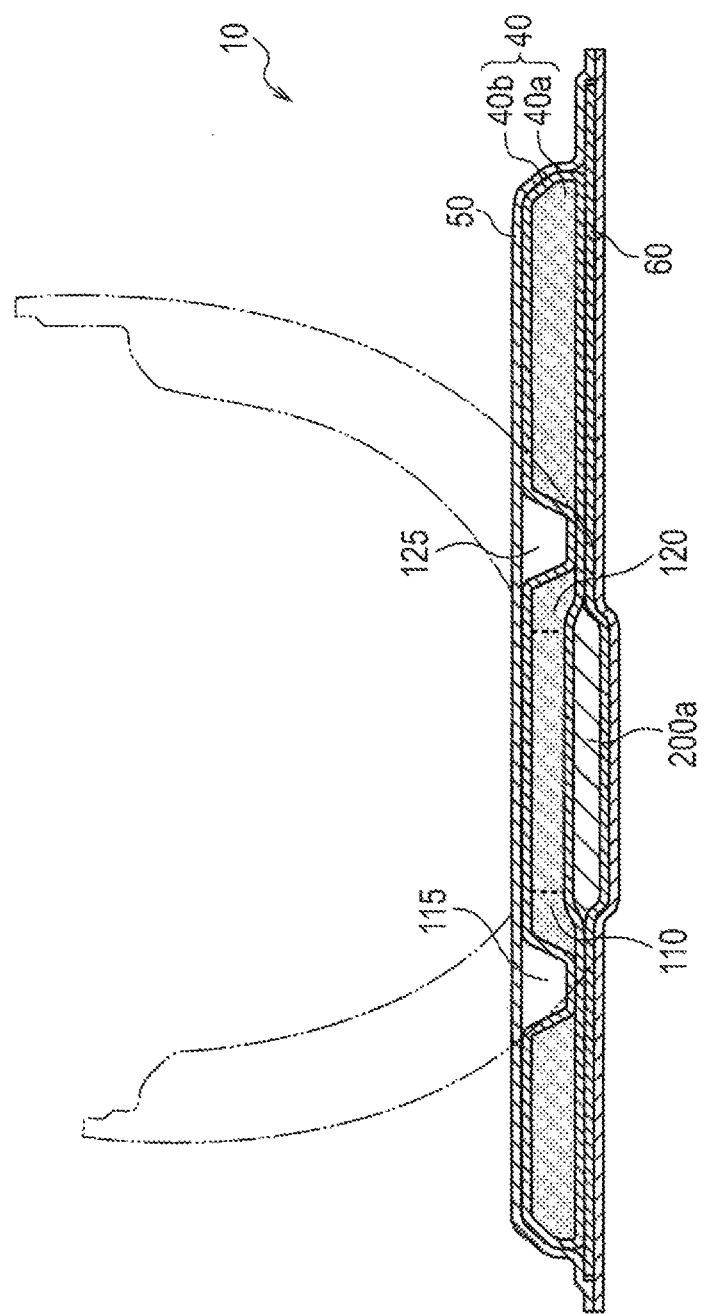
FIG. 2 is a cross-sectional view of the disposable diaper 10 along an F2-F2 line shown in FIG. 1.

FIG. 2 is a cross-sectional view of the disposable diaper 10 along an F2-F2 line shown in FIG. 1.

As illustrated in FIG. 1 or FIG. 2, the disposable diaper 10 includes a front waistline region 20, a crotch region 25, and a rear waistline region 30. The front waistline region 20 is a portion that is in contact with the front waistline unit of the wearer. Furthermore, the rear waistline region 30 is a portion that is in contact with the rear waistline unit of the wearer. The crotch region 25 is positioned between the front waistline region 20 and the rear waistline region 30. Furthermore, a pair of leg hole opening units 35 (see FIG. 4) is formed in the disposable diaper 10.

In the present embodiment, the direction from the front waistline region 20 to the rear waistline region 30 is called the product longitudinal direction L, and the direction perpendicular to the product longitudinal direction L is called the product widthwise direction W.

The disposable diaper 10 includes an absorber 40 running across the crotch region 25 and extending towards the front waistline region 20 and the rear waistline region 30. The absorber 40 is configured by an absorbent core 40a and a core wrap 40b.

The absorbent core 40a is same as in the conventional disposable diaper, and can be configured appropriately by using popular components and materials, such as ground pulp and high absorbent polymer. The absorbent core 40a is wrapped by the sheet-like core wrap 40b. The core wrap 40b is a sheet for wrapping the absorbent core 40a. A part of at least the skin surface side of the core wrap 40b is configured by various nonwoven fabrics or a tissue sheet having permeability. For example, an air-through nonwoven cloth, a spunbond nonwoven cloth, or an SMS (spunbond-meltblown-spunbond) nonwoven cloth having a mass of approximately 10 to 30 g/m$^2$, or a tissue sheet having a mass of approximately 10 to 30 g/m$^2$ can be used.

On the top side (skin contact surface side) of the absorber 40 is provided the liquid-permeable topsheet 50. Furthermore, on the back side (non-skin contact surface side) of the absorber 40 is provided a liquid-impermeable backsheet 60.

A side flap 70 is provided in each side edge in the product widthwise direction W of the absorber 40. The side flaps 70 are made of one or two or more pieces of nonwoven fabrics overlapping one another. Furthermore, a fastening tape 90 is provided in each of the pair of side flaps 70.

The fastening tape 90 extends along the product widthwise direction W in the front waistline region 20 and the rear waistline region 30, and holds the disposable diaper 10 onto the body of the wearer. In the present embodiment, the waistline retaining unit is configured by the front waistline region 20, the rear waistline region 30, and the fastening tape 90.

The top side (topsheet 50 side) of the absorber 40 includes a left- and right pair of the leg gathers 75 formed by an elastic nonwoven sheet. At least in the crotch region 25, the nonwoven sheet is preferred to have a width of 5 mm (width in the product widthwise direction W in the natural state of the disposable diaper 10) or more and 35 mm or less. When the width is less than 5 mm, the effect of the sheet running, substantially on its surface, along the area around the legs of the wearer is not exhibited, and if the width exceeds 35 mm, the region along the area around the legs widens as a result of which the nonwoven sheet may easily shift in towards the body of the wearer or may turn over.

The size (length) in the natural state implies that the disposable diaper 10 is taken out of the package, and a spring measure manufactured by Shinwa Rules Co., Ltd. (tape: covered with glass fiber reinforced vinyl chloride) is used to measure 10 samples that have been kept for 12 hours in an ambient temperature of 20° C.±2° C., and a relative humidity of 60%±5% RH. by placing the spring measure along the area to be measured. Furthermore, a pair of leg side gathers 80 extending along the product longitudinal direction L have been provided on the inner side of the pair of leg gathers 75 (towards the center of the product widthwise direction W). The disposable diaper 10 may also include waist gathers arranged along the product widthwise direction W in the front waistline region 20 and the rear waistline region 30.

A first inflected unit 110 and a second inflected unit 120 are formed in the absorber 40. The first inflected unit 110 and the second inflected unit 120 extend along the product widthwise direction W. The second inflected unit 120 is positioned towards the rear waistline region 30 from the first inflected unit 110. The first inflected unit 110 and the second inflected unit 120 form the curved base points of the disposable diaper 10.

The crotch unit 200 is formed in the crotch region 25, specifically, between the first inflected unit 110 and the second inflected unit 120. The crotch unit 200 is formed so as to more easily maintain the flat shape as compared to the other portions of the absorber 40. The crotch unit 200 includes the crotch stretch unit 200a that can be expanded and contracted in at least the product longitudinal direction L or the product widthwise direction W. That is, the first inflected unit 110 and the second inflected unit 120 are formed by the rigidity difference between the area contracted by the contraction of the crotch stretch unit 200a and the area other than the contracted area. Therefore, as described later, a flat "bottom unit" is formed in the disposable diaper 10.

In the present embodiment, a notch 115 (notch 125) is formed in the region outside the product longitudinal direction L of the first inflected unit 110 (second inflected unit 120). The notch 115 is formed in a region corresponding to the first inflected unit 110. Similarly, the notch 125 is formed in a region corresponding to the second inflected unit 120. The notch 115 and the notch 125 is a region in which the absorbent core 40a configuring the absorber 40 does not exist. In the present embodiment, the notch 115 and the notch 125 correspond to a low rigidity unit in which the basis weight of the absorbent core 40a are lower than that of the other portion of the absorbent core 40a. It should be noted that instead of forming the notch 115 and the notch 125, the region of the notch 115 and the notch 125 may be such that the basis weight of the absorbent core 40a is lower than that of the other portion of the absorbent core 40a.

For example, it should be noted that the basis weight of the absorbent core 40a of each portion can be measured by the following measurement method.

Firstly, open a package wrapping the disposable diaper 10, spread the folded disposable diaper 10, and measure dimensions of the measurement-target portion of which the basis weight is to be measured.

Secondly, cut the measurement-target portion out of the disposable diaper 10, take the portion other than the absorbent core 40a such as a topsheet and backsheet off the cut portion, and measure the weight of the absorbent core 40a.

Thirdly, calculate the basis weight of the absorbent core 40a of the measurement-target portion, based on the measured weight of the absorbent core 40a and the dimensions of the measurement-target portion.

The notch 115 and the notch 125 are formed in order to improve the condition of the first inflected unit 110 and the second inflected unit 120. In the present embodiment, the notch 115 and the notch 125 exist along the edges in the product longitudinal direction L of the crotch unit 200. It should be noted that even though the notch 115 and the notch 125 are formed, the absorbent core 40a positioned in the front waistline region 20 and the rear waistline region 30, and the absorbent core 40a positioned in the crotch region 25 are preferred to be in continuation rather than being completely separate.

As the notch 115 and the notch 125 run towards the outer side of the product widthwise direction W, the length in the product longitudinal direction L keeps on widening. As a result of such a shape, the outer side of the product widthwise direction W of the absorbent core 40a can contract easily, and thus, as described later, a flat "bottom unit" is formed in the disposable diaper 10. Furthermore, the absorbent core 40a positioned towards the front waistline region 20 from the notch 115, and the absorbent core 40a positioned towards the rear waistline region 30 from the notch 125 rise up from the "bottom unit", and can easily curve along the roundness of the body of the wearer (the abdomen and the hip).

The edge towards the front waistline region 20 (rear waistline region 30) of the notch 115 (notch 125) is arc shaped. The shape of the edge of the notch 115 (notch 125) is such that the center of the arc is positioned in the rear waistline region 30 (front waistline region 20) from the edge. As a result of such a shape, the deformation along the roundness of the body of the wearer occurs more easily and remarkably.

Rather than intersecting the front waistline region 20, the rear waistline region 30, and the fastening tape 90 that configure the waistline retaining unit, the crotch unit 200 is provided independently from the front waistline region 20, the rear waistline region 30, and the fastening tape 90.

(2) Shape of Crotch Unit

Figure 3:
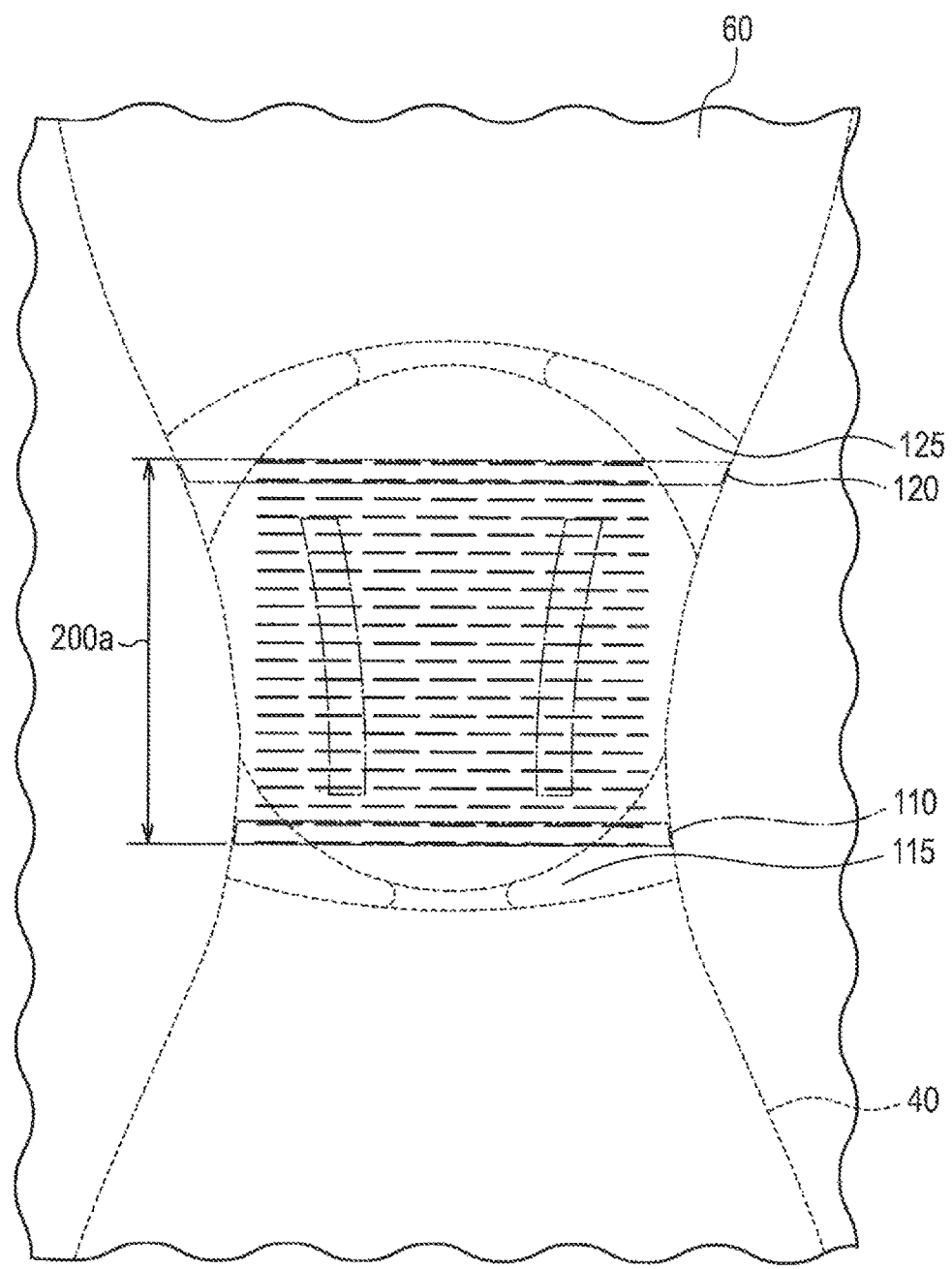
FIG. 3 is a magnified plan view of a crotch unit 200 according to the embodiment of the present invention, as seen from the backsheet 60 side.

Next, the shape of the crotch unit 200 will be described. FIG. 3 is a magnified plan view of the crotch unit 200 as seen from the backsheet 60 side.

As described above, the crotch unit 200 includes the crotch stretch unit 200a. In the present embodiment, an elastic sheet is used as the crotch stretch unit 200a. A stretch film formed by melting a thermoplastic elastomer resin, such as urethane and styrene, and then converting into the shape of a film, a nonwoven fabric formed from such elastic fibers, or a composite sheet formed by pasting together non-elastic sheets that have been partially cut into a stretch film and elastic nonwoven fabric, or have been made fragile can be used as the elastic sheet.

Furthermore, rather than an elastic sheet, the crotch stretch unit 200a can also be configured through an alternate, parallel arrangement of thread-like or band-like stretchable elastic members made from polyurethane elastic fibers and natural rubber. In such a case, in view of the rigidity of the absorbent core 40a and the rigidity of the other members configuring the disposable diaper 10, the thickness of the elastic members and the arrangement pitch can be selected appropriately, however, when the main body of the disposable diaper 10 is in the natural state (un-expanded state), the entire side edge region in the product widthwise direction W of the absorbent core 40a is preferable to be in a constricted state.

In the present embodiment, the crotch unit 200 can be expanded and contracted along the product longitudinal direction L. As a result, the front waistline region 20 and the rear waistline region 30 can rise up easily due to the constriction of the crotch unit 200, thus improving the fitting of the disposable diaper 10 on the wearer. Specifically, the rate of expansion and contraction of the crotch unit 200 is set 1.2 times or more and 1.8 times or less.

The rate of expansion and contraction of the crotch unit 200 implies the extent of expansion and contraction of the crotch unit 200 in the direction of expansion and contraction (product longitudinal direction L), and is stipulated as below:

The rate of expansion and contraction of crotch unit 200=(Length of the crotch unit during maximum extension)/(Length of the crotch unit in the natural state)

It should be noted that the rate of expansion and contraction of the crotch unit 200 is measured as described below.

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the crotch unit 200 when the disposable diaper 10 is in the natural state, and the length of the crotch unit 200 when the disposable diaper 10 is extended from its natural state until wrinkles caused by the elastic members are not visible to the naked eye.

The above measurement was performed for 10 samples, and the average value was assumed as the aforementioned length.

As a result of such a rate of expansion and contraction, it is possible to favorably follow the expansion and contraction of the skin of the wearer. This is because when the skin of the wearer expands and contracts, for example, when a slouchy posture is adopted where the front side of the body contracts in the hip of the wearer, the skin in the hip expands by approximately 30% as compared to the state when the body has been expanded.

That is, when the rate of expansion and contraction is 1.2 times or less, the constriction in the natural state of the disposable diaper 10 is insufficient, and as compared to non-contraction, the difference in the ease of curving of the disposable diaper 10 is small because of which the first inflected unit 110 and the second inflected unit 120 are not formed at the desired position. On the other hand, when the rate of expansion and contraction is more than 1.8 times, the contraction size in the contraction direction of the crotch stretch unit 200a becomes too large, the region where the crotch stretch unit 200a exists (crotch stretch unit 200a) easily comes in close contact with the body of the wearer rather than running along it because of which the disposable diaper 10 easily shifts to the lower side of the wearer.

The size of the crotch unit 200 along the product longitudinal direction L is 30 mm or more and 150 mm or less in the natural state of the disposable diaper 10. When the wearer is made to lie down on his/her back on a level bed, and an observation is made from the side of the wearer, the size of the crotch unit 200 is preferable so that the abdominal side passes through the belly button of the wearer and at the same time does not come in contact with an imaginary line parallel to the bed top, and the dorsal side fits into the crotch of the wearer without coming in contact with the bed.

When the size is less than 30 mm, the crotch unit 200 cannot sufficiently cover the crotch of the wearer, and it becomes difficult for the crotch unit 200 to come close to the body of the wearer. On the other hand, when the size exceeds 150 mm, it becomes difficult for the crotch unit 200 to fit within the crotch of the wearer. Because the disposable diaper 10 is held in place by the region around the waistline in the abdominal side and dorsal side of the wearer, when the crotch unit 200 extends in the region, the crotch stretch unit 200a comes in close contact with the body of the wearer due to the contractile force of the crotch stretch unit 200a. When the crotch stretch unit 200a comes in close contact with the body of the wearer, it becomes difficult for a bodily waste retaining space to form between the body and the disposable diaper 10. This is also not preferable because the disposable diaper 10 can easily shift towards the lower side due to the movement of the wearer.

Furthermore, the crotch unit 200 is formed at a position that includes the center of the disposable diaper 10 in the product longitudinal direction L. Furthermore, the length of the rear waistline region 30 in the product longitudinal direction L in the natural state of the disposable diaper 10 is longer than the length of the front waistline region 20 in the product longitudinal direction L in the natural state of the disposable diaper 10.

Specifically, the ratio of the length of the rear waistline unit in the product longitudinal direction with the length of the front waistline unit in the product longitudinal direction is 1.1 or more and 1.6 or less, and more preferably is 1.2 or more and 1.5 or less. If the ratio exceeds 1.6, the balance between the abdominal side and dorsal side of the disposable diaper 10 is disturbed, and when the crotch unit 200 of the diaper runs along the crotch region 25, the front waistline region 20 comes in very close contact with the body, and the rear waistline region 30 is covered by more than the required amount. Specifically, because the hip of the body of the wearer is generally protruding out more than the lower abdomen, by matching the crotch unit 200 with the crotch of the wearer, and then setting the ratio within the aforementioned range, the disposable diaper 10 seems to have a more suitable shape for complex body shapes. That is, the partial stiffness of the disposable diaper 10 due to the occurrence of a portion with an insufficient size, and the unnecessary space between the disposable diaper 10 and the body of the wearer due to the occurrence of a portion with an excess size can be prevented.

Furthermore, particularly in the case of an infant or toddler who is in the stage prior to walking, or has just started walking, the body is preferably bent towards the abdominal side with a rounded posture. In such a posture, the skin of the hip expands easily, and by setting the ratio within the aforementioned range, the disposable diaper will become suitable for the body of an infant or toddler that easily takes such a posture.

As an example, in the natural state of the disposable diaper 10, the front waistline region 20 is set to 130 mm, the crotch unit 200 is set to 80 mm, and the rear waistline region 30 is set to 190 mm with respect to the product length of 400 mm (product longitudinal direction L) of the disposable diaper 10. In such a case, the ratio of the length of the front waistline region 20 with the length of the rear waistline region 30 is approximately 1.46. By setting such a ratio, not only the crotch unit 200, but the entire product longitudinal direction L of the disposable diaper 10 can further be set along the body of the wearer.

In the present embodiment, the width of the crotch stretch unit 200a in the product widthwise direction W in the natural state of the disposable diaper 10 and the width of the absorbent core 40a in the crotch stretch unit 200a in the natural state of the disposable diaper 10 are almost the same in at least one part. "Almost the same" implies that the difference in the width between the absorbent core 40a and the crotch stretch unit 200a in the natural state of the disposable diaper 10 with respect to the width of the absorbent core 40a in the natural state of the disposable diaper 10 is within 20%.

Specifically, the width of the crotch stretch unit 200a in the product widthwise direction W in the natural state of the disposable diaper 10 is preferably between 50 and 110 mm, and more preferably 90 mm or less. In the present embodiment, the width of the absorbent core 40a along the product widthwise direction W in the natural state of the disposable diaper 10 is the narrowest in the region where the crotch unit 200 is formed.

If the width of the crotch stretch unit 200a is too narrow as compared to the absorbent core 40a, the effect of maintaining the crotch stretch unit 200a in a flat shape is difficult to exhibit. On the other hand, if the width of the crotch stretch unit 200a is too wide, the region in which the absorbent core 40a is not arranged gets contracted, and the rigidity on the outer side in the widthwise direction of the crotch stretch unit 200a increases. Therefore, the crotch stretch unit 200a may be caught easily in the femur of the wearer. Furthermore, because the diaper is worn in a state where the crotch stretch unit 200a is relatively contracted in a region where the absorbent core 40a does not exist, overlapping of members may occur easily and the crotch stretch unit 200a may harden as a result of which the wearing comfort may be missed out.

Furthermore, the distance between the absorbent core 40a in the crotch stretch unit 200a and the inner ends in the product widthwise direction W of the leg gathers 75, in the natural state of the disposable diaper 10, is preferably between 30 and 60 mm. As a result, the crotch stretch unit 200a can easily come close to the body of the wearer by the leg gathers 75, and furthermore, the crotch stretch unit 200a can come close to the body of the wearer while maintaining an appropriate gap.

Additionally, in the natural state of the disposable diaper 10, the width of the crotch unit 200, specifically, the crotch stretch unit 200a, along the product widthwise direction W, is narrower than the width of the absorbent core 40a along the product widthwise direction W in a region overlapping the crotch unit 200.

However, in the natural state of the disposable diaper 10, the difference between the width of the crotch unit 200 along the product widthwise direction W and the width thereof along the product widthwise direction W in the portion having the narrowest width of the absorbent core 40a in the region overlapping the crotch unit 200 is 20% or less.

Furthermore, in the natural state of the disposable diaper 10, the portion where the width of the absorbent core 40a in the crotch unit 200 is the narrowest is arranged at a position that is 10 to 60 mm towards the front waistline region 20, and preferably at a position that is 20 to 40 mm towards the front waistline region 20 from the central line of the disposable diaper 10 along the product widthwise direction W, and the crotch stretch unit 200a is preferably arranged across this area. The position at which the left and the right femurs are closest to each other is towards the front waistline from the center in the front-and-rear direction of the body of the wearer. Therefore, by having an arrangement as described above, the inflected units can be provided at a position matching more the shape of the body, the absorbent core 40a can be arranged, and the crotch unit 200 can be made to run along the crotch of the wearer while improving the wearing comfort.

(3) Operation and Effect

Figure 4:
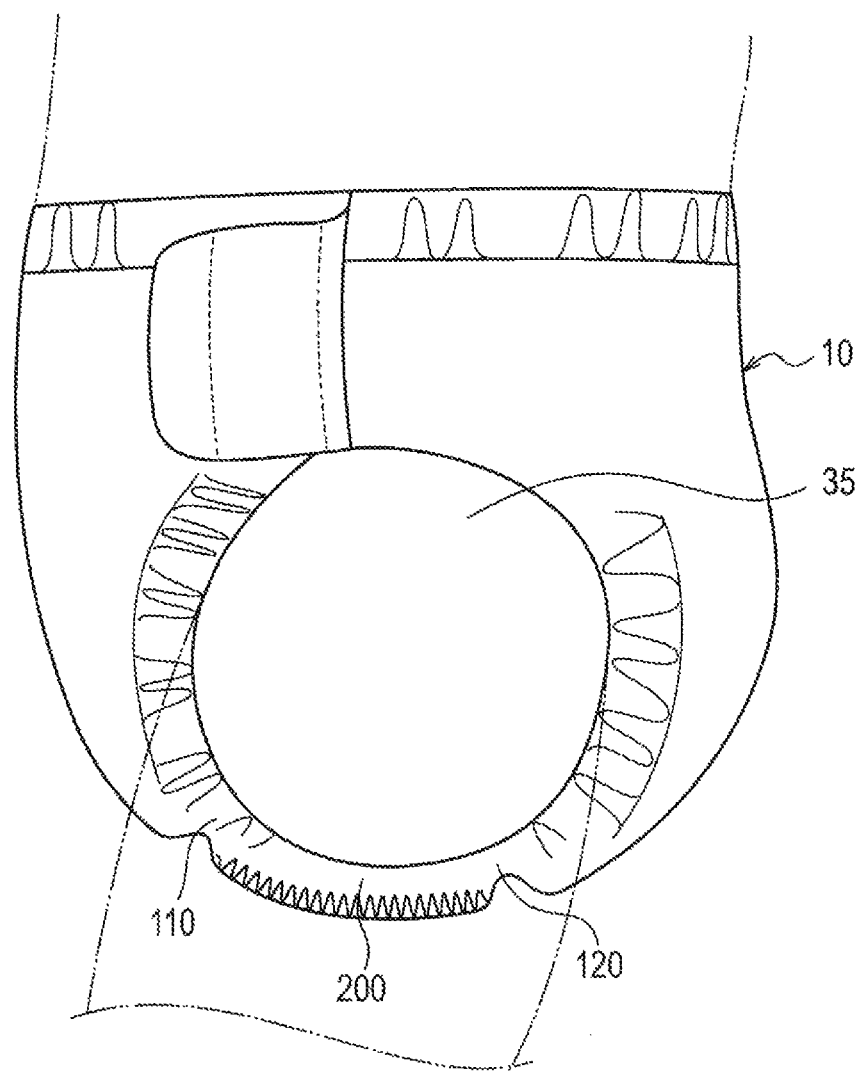
FIG. 4 is a diagram schematically illustrating the state when the disposable diaper 10 according to the embodiment of the present invention is worn by a wearer.

Next, the operation and effect of the disposable diaper 10 will be described. FIG. 4 is a diagram schematically illustrating the state when the disposable diaper 10 is worn by a wearer. FIGS. 5(a) and (b) are diagrams schematically illustrating the result of a CT scan of the state when the disposable diaper 10 and the conventional disposable diaper are worn by a wearer.

As illustrated in FIG. 4 and FIG. 5, while the disposable diaper 10 bends with the first inflected unit 110 and the second inflected unit 120 as the origin, the crotch stretch unit 200a is provided in the crotch unit 200 because of which a flat shape is easily maintained, and as a result, the crotch unit 200 forms an almost flat "bottom unit" immediately below the crotch (inner leg) of the wearer. That is, because the crotch stretch unit 200a is arranged in the crotch unit 200, the disposable diaper 10 inflects (bends) at the boundary between the stretching unit and the un-stretching unit.

FIG. 5(a) illustrates the result when a CT image is taken of the state of wearing the disposable diaper 10 by the wearer, and when the disposable diaper 10 is compared with the conventional disposable diaper illustrated in FIG. 5(b) in which the crotch stretch unit 200a is not provided, it is clear that in the state of wearing the diaper, a crotch unit 200 having a shape close to a flat shape is formed.

Specifically, inflected units (the first inflected unit 110 and the second inflected unit 120) are formed near each boundary between the crotch unit 200 and the abdominal side, and the crotch unit 200 and the dorsal side, because of which as compared to the conventional disposable diaper, the extent of bending (change in the angle of curving) from the abdominal side to the crotch region, and from the dorsal side to the crotch region becomes relatively remarkable. As a result, the abdominal side and the dorsal side of the disposable diaper 10 are held close to the body of the wearer, and the crotch unit 200 is arranged at a position closer to the body, which enables the crotch unit 200 to run along the body of the wearer without sagging down.

Furthermore, because the disposable diaper 10 bends with the first inflected unit 110 and the second inflected unit 120 as the origin, two apexes, that is, each apex at the front waistline side and that at the rear waistline side, are formed, and the almost flat crotch unit 200 is positioned between the two apexes.

According to such a disposable diaper 10, because of an almost flat crotch unit 200, the crotch unit 200 can be brought close to the body of the wearer while maintaining an appropriate space with the body of the wearer, and the comfort and absorption performance after excretion can be maintained. Furthermore, a wearing comfort as if to wear the underwear, specifically, a pleasant feeling of wearing the diaper, without hindering the movement of the wearer, can be achieved. That is, by clearly providing a gusset unit (bottom unit), and sterically making the disposable diaper 10 run along the body of the wearer, the excess tightening due to elastic members is reduced in the disposable diaper 10. In other words, in a disposable diaper 10 in which such a "bottom unit" is formed, because the crotch unit 200 comes close to the body, the disposable diaper can be made to fit without tightening the leg holes, and the crotch unit exists in the original meaning (the front waistline region 20, the crotch region 25, and the rear waistline region 30 can be made to run along the body).

On the other hand, in the conventional disposable diaper, because only the front body and rear body exist essentially, when the disposable diaper is worn, it is easy for the crotch unit to exist at a position towards the lower side from the crotch of the wearer. As a result, the absorber is to exist far below a location where it is stuck between the left and right femurs of the wearer. In such a case, the absorber stuck between the femurs of the wearer follows the movement of the legs of the wearer, and moves in all four directions, due to which the fibers and high absorbent polymer constituting the absorber shift towards the center. When the fibers and high absorbent polymer constituting the absorber shift towards the center, the space between the crotch of the wearer and the crotch unit of the disposable diaper is filled, due to which the space for retaining the bodily waste becomes smaller and the density of the absorber in the crotch increases thus causing the absorption speed to decline, which poses a problem. Such a problem can be resolved by the disposable diaper 10.

Furthermore, when rompers, which are frequently worn by infants and small children, are used, then at the time of locking the front waistline side and the rear waistline side with a hook, in the inner leg unit of the romper, the crotch unit of the disposable diaper would become a hindrance, however, according to the disposable diaper 10, as the crotch unit 200 does not shift away by more than the required amount from the crotch of the wearer, when the disposable diaper is worn, such a problem can be resolved.

(4) Other Embodiments

So far, the present invention is disclosed through the above embodiment. However, it should not be interpreted that the statements and drawings constituting a part of the present disclosure limit the present invention. From this disclosure, a variety of alternate embodiments, examples, and applicable techniques will become apparent to one skilled in the art.

For example, the embodiment of the present invention can be modified as follows. FIG. 6 and FIG. 7 illustrate the shape of the crotch unit of the disposable diaper according to modifications of the present invention.

In the disposable diaper 10A illustrated in FIG. 6, a dart unit 220 is formed rather than the crotch stretch unit 200a. The dart unit 220 is formed in the edge of the crotch unit 200 in the product longitudinal direction L. In the example illustrated in FIG. 6, the four dart units 220 are formed, however, the number of the dart units 220 may be more than four. Alternatively, the number of the dart units 220 may be lesser than four, but from the viewpoint of easily retaining the crotch unit 200 in a flat shape, the four or more dart units are desired.

The dart unit 220 is the portion that picks a part of the exterior sheet arranged on the non-skin contact surface side of the absorber 40, and in the present modification, the backsheet 60. In the present modification, the distance between the outer positions in the product widthwise direction W where the dart units 220 are formed is the width of the dart units 220. As a result of formation of the dart units 220, it becomes easy for the crotch unit 200 that is positioned towards the inner side from the dart unit 220 to take a flat shape. That is, the same effect as the aforementioned disposable diaper 10 can be realized even by the disposable diaper 10A.

In the disposable diaper 10B illustrated in FIG. 7, a reinforcing sheet 230 is formed rather than the crotch stretch unit 200a. In the present modification, the distance between the outer positions in the product widthwise direction W where the reinforcing sheets 230 are formed is the width of the reinforcing sheets 230. The reinforcing sheets 230 have the function of reinforcing the crotch unit 200 and improving the rigidity. As a result, the crotch unit 200 can easily be formed in a flat shape, and the first inflected unit 110 and the second inflected unit 120 are formed in the boundary between the regions where the reinforcing sheets 230 exist and where the reinforcing sheets 230 do not exist as a result of the contractile force of the leg gathers 75 extending in the product longitudinal direction L, and therefore, the same effect as the aforementioned disposable diaper 10 can be realized even by the disposable diaper 10B. Furthermore, by making the edges of the abdominal side and dorsal side of the reinforcing sheets 230 in the shape of an arc so as to form a convex shape towards the abdominal side and the dorsal side, the front waistline region and the rear waistline region of the disposable diaper 10B get curved, and can easily run along the roundness of the body of the wearer.

Furthermore, in the aforementioned disposable diaper 10, in order to make the expansion and contraction of the crotch unit 200 easy to recognize visually, a portion colored in a color different from the surroundings, or a motif may be displayed in the topsheet 50 or the backsheet 60 of the crotch unit 200. For example, in FIG. 3, the region indicated by a dashed line may be colored in a color different from the surroundings.

In the aforementioned embodiment, the formation of the notch 115 and the notch 125, or the fact that in the region of the notch 115 and the notch 125, the basis weight of the absorbent core 40a is lower than that of the other portion of the absorbent core 40a has been described, however, it is not necessary to have such a structure. That is, the notched units, or the portion of the absorbent core 40a with the low basis weight need not necessarily be present.

Furthermore, in the disposable diaper according to the present modification, rather than leg gathers formed from an elastic nonwoven sheet, leg gathers formed from thread-like elastic members may be provided.

In the aforementioned embodiment, an open-type disposable diaper in which the fastening tape 90 has been provided was described as an example, however, the present invention is also applicable to a pant-type disposable diaper. As regards a pant-type diaper having a waistline opening unit and a pair of leg hole opening units formed by joining both left-right edges of an outer-layer sheet forming the front waistline region and the rear waistline region, the outer-layer sheet of the front waistline region and the rear waistline region includes elastic elements that can be expanded and contracted in the product widthwise direction W, and by contracting the elastic elements, the disposable diaper is held in the waistline of the wearer. That is, the area in which both left-right edges extending in the product longitudinal direction L are joined becomes the waistline retaining unit.

As described above, it is of course that the present invention includes various embodiments and the like not described here. Therefore, the technical range of the present invention is to be defined only by the inventive specific matter according to the adequate claims from the above description.

REFERENCE SIGNS LIST 10, 10A, 10B Disposable diaper
20 Front waistline region
25 Crotch region
30 Rear waistline region
35 Leg hole opening unit
40 Absorber
40a Absorbent core
40b Core wrap
50 Topsheet
60 Backsheet
70 Side flap
75 Leg gathers
80 Leg side gathers
90 Fastening tape
110 First inflected unit
115 Notch
120 Second inflected unit
125 Notch
200 Crotch unit
200a Crotch stretch unit
220 Dart unit
230 Reinforcing sheet

The invention claimed is:
1. A disposable diaper, comprising:
a front waistline region;
a rear waistline region;
a crotch region positioned between the front waistline region and the rear waistline region;
a pair of leg hole opening units;
an absorber running across the crotch region and extending in the front waistline region and rear waistline region;
a product longitudinal direction from the front waistline region towards the rear waistline region;
a product widthwise direction that is perpendicular to the product longitudinal direction;
a pair of leg elastic members opposing each other in the product widthwise direction;
a waistline retaining unit extending along the product widthwise direction in the front waistline region and the rear waistline region, and adapted to hold the disposable diaper onto a body of a wearer;
a crotch stretch unit arranged in the crotch region and configured to be expanded and contracted in the product longitudinal direction or the product widthwise direction;
a first inflected unit arranged in the absorber and defining a first curved base point of the disposable diaper by extending along the product widthwise direction; and
a second inflected unit arranged in the absorber and defining a second curved base point of the disposable diaper by extending along the product widthwise direction, the second inflected unit being positioned between the rear waistline region and the first inflected unit;

wherein
the crotch stretch unit is provided independently from the waistline retaining unit without intersecting the waistline retaining unit,
the crotch stretch unit does not intersect the leg elastic members in a plan view of the disposable diaper,
a length of the crotch stretch unit in the product longitudinal direction is 30 mm or more and 150 mm or less, in a natural state of the disposable diaper,
the absorber includes an absorbent material, and
the first and second inflected units include parts of the absorbent material.

2. The disposable diaper according to claim 1, wherein the crotch stretch unit is configured to be expanded and contracted along the product longitudinal direction.

3. The disposable diaper according to claim 1, wherein a ratio of expansion and contraction of the crotch stretch unit is 1.2 times or more and 1.8 times or less.

4. The disposable diaper according to claim 1, wherein the absorber includes a low rigidity unit in which
an absorbent core including the absorbent material and configuring the absorber does not exist, or
a basis weight of the absorbent core is lower than that of the other portion of the absorbent core,
the crotch stretch unit has longitudinal edges opposing each other in the product longitudinal direction, and
the low rigidity unit is formed at the longitudinal edges of the crotch stretch unit.

5. The disposable diaper according to claim 4, wherein
the absorber includes a notch in which the absorbent core configuring the absorber does not exist,
a dimension of the notch in the product longitudinal direction is increased as the notch extends towards an outer side of the absorber in the product widthwise direction, and
the notch has edges each in a shape of an arc and curving towards the front waistline region or the rear waistline region.

6. The disposable diaper according to claim 4, wherein
a width of the absorbent core configuring the absorber along the product widthwise direction is narrowest in a region where the crotch stretch unit is arranged.

7. The disposable diaper according to claim 4, wherein
the absorber has a region overlapping the crotch stretch unit in a product thickness direction that is perpendicular to the product widthwise direction and the product longitudinal direction,
a width of the crotch stretch unit in the product widthwise direction is narrower than a width of the region of the absorber in the product widthwise direction,
the region of the absorber includes a portion having a narrowest width of the absorbent core in the product widthwise direction, and
a difference between the width of the crotch stretch unit along the product widthwise direction and the width of the portion having the narrowest width of the absorbent core is 20% or less.

8. The disposable diaper according to claim 4, wherein
at least one part of the first inflected unit and the second inflected unit has a basis weight lower than that of the other portion of the absorbent core, or is free of the absorbent core.

9. The disposable diaper according to claim 1, wherein
the crotch stretch unit is arranged at a position including a center of the disposable diaper in the product longitudinal direction, and
a length of the rear waistline region in the product longitudinal direction is greater than a length of the front waistline region in the product longitudinal direction.

10. The disposable diaper according to claim 9, wherein
a ratio of the length of the rear waistline region in the product longitudinal direction to the length of the front waistline region in the product longitudinal direction is 1.1 or more and 1.6 or less.

11. The disposable diaper according to claim 1, wherein
the crotch stretch unit overlaps the absorbent material in a product thickness direction perpendicular to the product widthwise direction and the product longitudinal direction.

12. The disposable diaper according to claim 1, wherein
the first inflected unit and the second inflected unit are formed by a rigidity difference between (i) a first area contracted by the contraction of the crotch stretch unit and (ii) a second area other than said first area and contracted by the contraction of the crotch stretch unit.

13. A disposable diaper comprising:
a front waistline region;
a rear waistline region;
a crotch region positioned between the front waistline region and the rear waistline region;
a pair of leg hole opening units;
an absorber running across the crotch region and extending in the front waistline region and rear waistline region;
a product longitudinal direction from the front waistline region towards the rear waistline region;
a product widthwise direction that is perpendicular to the product longitudinal direction;
a pair of leg elastic members opposing each other in the product widthwise direction;
a waistline retaining unit extending along the product widthwise direction in the front waistline region and the rear waistline region, and adapted to hold the disposable diaper onto a body of a wearer;
a crotch stretch unit arranged in the crotch region and configured to be expanded and contracted in the product longitudinal direction or the product widthwise direction;
a first inflected unit arranged in the absorber and defining a first curved base point of the disposable diaper by extending along the product widthwise direction; and
a second inflected unit arranged in the absorber and defining the curved base point of the disposable diaper by extending along the product widthwise direction, the second infected unit being positioned between the rear waistline region and the first inflected unit;
wherein
the crotch stretch unit does not intersect the leg elastic members in a plan view of the disposable diaper,
the absorber is configured to bend along the first inflected unit and the second inflected unit,
when the disposable diaper is worn, as compared to other portions of the absorber, the crotch stretch unit maintains a flat shape,
the absorber includes an absorbent material, and
the first and second inflected units include parts of the absorbent material.

14. A disposable diaper comprising:
a front waistline region;
a rear waistline region;
a crotch region positioned between the front waistline region and the rear waistline region;

a pair of leg hole opening units;

an absorber running across the crotch region and extending in the front waistline region and rear waistline region;

a product longitudinal direction from the front waistline region towards the rear waistline region;

a product widthwise direction that is perpendicular to the product longitudinal direction;

a waistline retaining unit extending along the product widthwise direction in the front waistline region and the rear waistline region, and holding the disposable diaper onto a body of a wearer;

a crotch unit that is formed in the crotch region and can be expanded and contracted in the product longitudinal direction or the product widthwise direction;

a first inflected unit that is formed in the absorber and that becomes a curved base point of the disposable diaper by extending along the product widthwise direction; and a second inflected unit that is formed in the absorber, that becomes the curved base point of the disposable diaper by extending along the product widthwise direction, and that is positioned towards the rear waistline region from the first inflected unit;

wherein the crotch unit is provided independently from the waistline retaining unit without intersecting the waistline retaining unit, a size along the product longitudinal direction of the crotch unit is 30 mm or more and 150 mm or less, in a natural state of the disposable diaper, in the absorber, a low rigidity unit in which an absorbent core configuring the absorber does not exist or a basis weight of the absorbent core is lower than that of the other portion, is formed in a region of edges of the product longitudinal direction from the crotch unit, in the absorber, a notch in which the absorbent core configuring the absorber does not exist is formed, a length of the notch in the product longitudinal direction is configured to widen as the notch moves towards an outer side of the product widthwise direction, and edges of the notch towards the front waistline region or the rear waistline region are configured to be in a shape of an arc.

15. A disposable diaper comprising:
a front waistline region;
a rear waistline region;
a crotch region positioned between the front waistline region and the rear waistline region;
a pair of leg hole opening units;
an absorber running across the crotch region and extending in the front waistline region and rear waistline region;
a product longitudinal direction from the front waistline region towards the rear waistline region;
a product widthwise direction that is perpendicular to the product longitudinal direction;
a waistline retaining unit extending along the product widthwise direction in the front waistline region and the rear waistline region, and holding the disposable diaper onto a body of a wearer;
a crotch unit that is formed in the crotch region and can be expanded and contracted in the product longitudinal direction or the product widthwise direction;
a first inflected unit that is formed in the absorber and that becomes a curved base point of the disposable diaper by extending along the product widthwise direction; and
a second inflected unit that is formed in the absorber, that becomes the curved base point of the disposable diaper by extending along the product widthwise direction, and that is positioned towards the rear waistline region from the first inflected unit;
wherein
the crotch unit is provided independently from the waistline retaining unit without intersecting the waistline retaining unit,
a size along the product longitudinal direction of the crotch unit is 30 mm or more and 150 mm or less, in a natural state of the disposable diaper,
a width of the crotch unit along the product widthwise direction is narrower than a width of the absorber along the product widthwise direction in a region overlapping the crotch unit, and
a difference between the width of the crotch unit along the product widthwise direction and the width along the product widthwise direction in the portion having the narrowest width of an absorbent core configuring the absorber in the region overlapping the crotch unit is 20% or less.

* * * * *